United States Patent [19]

Shapiro

[11] Patent Number: 4,565,192
[45] Date of Patent: Jan. 21, 1986

[54] DEVICE FOR CUTTING A PATELLA AND METHOD THEREFOR

[76] Inventor: James A. Shapiro, 1460 N. Sandburg Ter., Chicago, Ill. 60610

[21] Appl. No.: 599,640

[22] Filed: Apr. 12, 1984

[51] Int. Cl.$^4$ .............................................. A61F 5/04
[52] U.S. Cl. ................................ 128/92 H; 128/92 E; 128/303 R
[58] Field of Search ................. 128/92 H, 92 R, 92 E, 128/92 EA, 92 EB, 303 R, 346

[56] References Cited

PUBLICATIONS

Richards, "RMC Total Knee System", 1983, pp. 14–20.
"Knee Replacement Using the Insall/Burstein Total Condylar Knee System", J. Insall, A. Burstein, p. 18, 1979.
Howmedica, "Total Condylar Prosthesis Surg. Tech.", Insall & Renawet, 1976, p. 3.
Zimmer, EFTEKHAR TM II Knee Prosthesis, Patellar Holder 8504–400, B–281, 5M281, 1980.

Primary Examiner—Gene Mancene
Assistant Examiner—C. W. Shedd
Attorney, Agent, or Firm—Marvin N. Benn; Milton Gerstein

[57] ABSTRACT

A device is disclosed for cutting a portion of a patella during knee surgery in which the articular surface of the patella along with a portion of the bone of the patella is cut away for implantation of a prosthesis. The device disclosed provides a fixed clamping member and an adjustable clamping member which clamp the patella and space from the patella a support surface for an oscillating saw used in the cutting of the patella. The precise plane of cut is provided by the use of a placement aid which is used according to the method of the present invention. The placement aid positions the support surface a precise depth below the articular surface of the patella during the clamping procedure, which clamping procedure also horizontally levels the support surface and the device so that all cuts through the patella are made in a perfectly horizontal plane. Spacers are also provided which are mountable over the support surface and are used to allow for progressively deeper cuts to be made in the patella through parallel horizontal planes of cut by allowing interchange of one spacer for another of less thickness. Each spacer has its own flat surface that allows support of the oscillating saw thereon for cutting through the patella during that particular cut as defined by the thickness of the spacer used.

27 Claims, 9 Drawing Figures

DEVICE FOR CUTTING A PATELLA AND METHOD THEREFOR

BACKGROUND OF THE INVENTION

The present invention is directed to a device for cutting a patella during knee surgery, such as total knee arthoplastic surgery. Due mainly to osteoarthritis (degenerative joint disease), though as well to other causes such as rheumatoid arthritis and trauma, the patella may need surgery, where the cartilage and some of the bone thereof are cut off and replaced by a prosthesis colloquially termed a "button". The prosthesis replaces the diseased cartilage and bone, and provides a new flat surface by which the patella with the prosthesis may be returned to its normal position against the femur.

The patella, commonly called kneecap, is that part of the human skeleton that is approximately 1.5-2 cm. in thickness having an articular surface of cartilage. The articular surface is held in place against the distal portion of the femur (the femoral condyles) by the patella tendon. The patella provides the leverage necessary for proper functioning of the knee joint. If the articular surface of the patella becomes damaged, or if the bone of the patella decays or is degenerative, proper functioning of the knee joint is not possible, with the concomitant pain and immobility associated therewith. If it be found that it is possible to replace a portion of the patella along with the articular surface in order to restore the knee joint to its normal functioning by providing the proper tensioning of the tendon holding the patella in place, surgery will be performed on the patella, during which the knee area is exposed and the patella everted such that the articular surface of cartilage is flipped over so that it faces away from the femoral condyles. After this has been achieved, the surgeon, as is the current practice, will direct an assistant to firmly hold the everted patella in place what are termed "towel clips", which actually resemble a pair of tongs that, in scissor-like fashion, can be operated to sandwich at its pointed tips the patella, at portions below the plane in which the surgeon is to cut the patella. The plane in which the surgeon will cut is preferably parallel to the flat articular surface of the patella and a desired distance therebelow, the distance being enough such that the prosthesis, or button, when implanted, will allow the patella to be approximately the same thickness as a normal, healthy patella, with due regard being directed to the age and size of the person whose patella is being fitted with the button and any special circumstances associated therewith.

The current practice among orthopedic surgeons is to choose the plane of cut of the patella by eye, and then, using a conventional oscillating saw, to cut through that plane to provide an approximately flat surface at a certain depth below the original articular surface that the surgeon feels will adequately accept the prosthesis and allow for proper functioning of the knee joint. After the surgeon has cut the patella through the plane and removed the diseased portions of the patella along with other bone, he next inserts the prosthesis by drilling a hole into the remainder of the patella bone. The prosthesis itself has a stem portion of 4 mm. depth, and integral therewith is the button having a depth of 9 mm. for a large person, and 8½ mm. for a small person. After the hole has been drilled, the stem is forced into the hole, thereby firmly implanting the prosthesis to the flat, cut and exposed surface of the patella. Thereafter, the surgeon will rotate the patella with implant 180 degrees to reposition it into its normal functioning location and orientation, with the surface of the botton now taking the place of the original articular surface of the patella.

It is common, however, that the surgeon, upon the repositioning of the patella with implant, will find that he has not removed enough of the patella to provide proper functioning of the knee joint and proper tensioning of the tendon holding the patella. Thus, the surgeon will evert the patella a second time, remove the implanted button with stem, and cut through the patella a second time in another plane, to thereby remove more of the patella. Then, he will again implant the prosthesis, and rotate the patella with implant a second time, to see if it now fits properly. This procedure is repeated as many times as it is necessary until the proper amount of patella has been removed to allow for implantation of the prosthesis and until the proper positioning and functioning of the patella with implant has been achieved.

Two requirements are essential to the above operation: good bone-to-prosthesis control, and enough patella left after cutting so that the stem of the prosthesis will have sufficient and proper anchorage. Since according to the way the cutting of the patella is presently carried out, which is by the surgeon's approximating where the plane of cut should be and then cutting therethrough by holding the oscillating saw in his hand, precise horizontal and flat surfaces are often not achieved, simply because of the guessing involved in determining the plane of cut, which must be horizontal and must be flat for proper fitting of the prosthesis and the proper functioning thereof.

Thus, the surgeon must be very careful and make a first cut in a plane that usually turns out not to have been deep enough. Further, when the surgeon repeats such steps, he again is very careful, only cutting off slightly below that plane in which he previously cut, thus ofttimes necessitating third, fourth or even more cuts, and the ensuing repositioning and eversions of the patella associated with each cut. Also, because the oscillating saw is hand-held, it is not uncommon for the surgeon to have cut the patella in a way that has not provided a flat surface necessary for the proper positioning of the prosthesis.

All of these above-noted disadvantages and drawbacks to the presently-used procedure for cutting the patella have caused excessive guessowrk to be employed in an operation requiring great skill, where cutting is required within extremely close tolerances, and have caused time-consuming operations because of the need to repeat the steps many times over, until the right cut is made. Further, it is also possible that, under presently-used techniques, too much bone may be cut off, if the surgeon is not extremely careful, thus dooming the knee operation to at least partial failure. In addition, the surgeon presently is in need of at least one assistant, who, utilizing the towel clips, firmly attaches them to the patella and holds the patella thereby. However, two assistants are often used for this purpose.

SUMMARY OF THE INVENTION

It is, therefore, the primary objective of the present invention to provide a novel device and method of using the device that will overcome the drawbacks and disadvantages of currently-used techniques of cutting off a portion of a patella for subsequent implantation thereto of a prosthesis in order to restore the diseased patella to normal functioning in the skeletal framework.

It is, also, the objective of the present invention to allow for cutting of the patella at a precise depth below the articular surface, such that the plane of cut is unmistakably in a horizontal plane, whereby the uneven and/or curved surfaces currently achieved with presently-used techniques are obviated.

It is, also, the objective of the present invention to provide a novel method and device for cutting a patella in a flat, horizontal plane, whereby additional parallel cuts of the patella may be made, after the first cut, in an easy, simple and precise manner.

It is, still, another objective of the present invention to provide a novel method and device for cutting a patella the necessary number of times to achieve the proper cut, so that the prosthesis fits and functions properly, such that the device remains attached to the patella for all cuts and during all intervals therebetween, and is not removed at all until the patella, with prosthesis implanted therein, is nestled into its proper location and found to be functioning properly.

It is, still, a further objective of the present invention to allow for the cutting of the patella at discreet depths below the articular surface thereof, where each discreet depth is readily and easily located by one simple step.

It is, still, another objective of the present invention to provide a device for cutting a patella in a plane parallel to the horizontal plane of the operating room's floor, such that the surgeon needs no assistance. In the present invention, the surgeon attaches the device to patella himself, and, thereafter, simply holds it in his hand via a handle, or the like, while cutting in the horizontal plane.

Toward the above ends, the present invention is provided with a pair of clamping members positioned in a diametrically-opposed relationship, so as to define therebetween a space in which a patella may be firmly held. One of the clamping members is adjustable toward and away from the other clamping member, which is fixed. Each clamping member is provided with a pair of pointed prongs for insertion into portions of the patella, one being on the medial side of the patella and the other being on the lateral aspect of the patella.

Each clamping member is mounted to one end of a support extension, the two extensions, in turn, being mounted at their other ends to a cutting guide surface used for supporting an oscillating saw, which is utilized to cut the patella in a horizontal plane parallel to the floor. The cutting guide surface is spaced from the clamping members a distance that allows for the extension of the blade of the oscillating saw. The top surface of the cutting guide surface is also slightly elevated from the tops of the clamping members to allow for cutting of the patella in a horizontal plane above the portions of the patella clamped by the clamping members. The cutting guide surface is provided with a level to ensure that its upper surface lies in a horizontal plane parallel to the floor, so that the plane of cut of the patella lies in a perfect horizontal plane. Alternatively, the level may be mounted in a diffferent portion of the device.

In order to position the cutting guide surface of the device at a proper depth below the articular surface of the patella, the present invention provides a placement aid that is mountable over the cutting guide surface, which placement aid has a depth preferably slightly less than the depth of the button, which is to be implanted to the cut patella. The placement aid has a projecting upper surface positioning portion that projects outwardly above and beyond the cutting guide surface toward the clamping members, such that the bottom of the positioning portion may touch the articular surface of the patella, to define a first distance below the articular surface. The present invention also provides a plurality of differently-sized spacers, ranging in thickness from one millimeter to 6 millimeters, though other ranges of thicknesses may also be provided. One of the spacers is initially mounted over the cutting guide surface between it and the placement aid, so that the upper surface of the spacer may be used for the first cut of the patella in a horizontal plane above that including the upper surface of the cutting guide surface. Since the placement aid preferably has a depth less than that of the prosthesis to be implanted, the upper surface of the spacer will provide for a first cut of the patella at a depth less than the depth of the prostheses, so that increased tensioning of the tendon may be had, which result is at times desired, depending upon the condition of the patella, as well as upon the condition of the tendon and related skeletal parts associated therewith. The spacer allows for an easy and fast method of achieving a precise second cut of the patella in another horizontal plane, which is achieved by simply removing the spacer and exposing the upper surface of the cutting guide surface, which may then be used as the support for the oscillating saw for the next cut. Alternatively, the spacer may be replaced with another spacer of smaller thickness, to allow for a cut in a horizontal plane below that which was used during the first cut.

As many cuts as desired may be made, with the only procedure required being simply replacing one spacer with another of smaller thickness, and continuing this procedure until the exact plane of cut is reached. Of course, between each cutting step, the patella along with the novel device of the present invention is rotated 180 degrees to position the patella back to its normal orientation against the femur, where it is determined if the proper cut has been made. If the proper cut has not been made, the patella, along with the device, is everted, where the next step of replacing the spacer is carried out, so as to allow for the cutting to be carried out in another horizontal plane below that in which the prior cut was made.

The fact that one of the clamping members is adjustable allows for the proper initial levelling of the device in a horizontal plane parallel to the floor. To level the device with the patella, all that is required is that, after the positioning portion of the placement aid bears upon the articular surface of the patella, the fixed clamping member is clamped to the patella. Thereafter, the device is tilted the proper amount until the level shows horizontal positioning of the cutting guide surface; thereafter, the adjustable clamping member is clamped to the patella, thus attaching the device to the patella in a horizontal plane. It is noted that the patella itself is first oriented so that the articular surface lies in a horizontal plane.

The placement aid and the spacers are mountable over the cutting guide surface preferably by a force fit with the cross brace, or the like, projecting from either end of the cutting guide surface, which cross brace connects the cutting guide surface to the other ends of the extensions from the clamping members.

BRIEF DESCRIPTION OF THE DRAWING

The invention will be more readily understood with reference to the accompanying drawing, wherein.

DETAILED DESCRIPTION OF THE INVENTION

Figure 1:
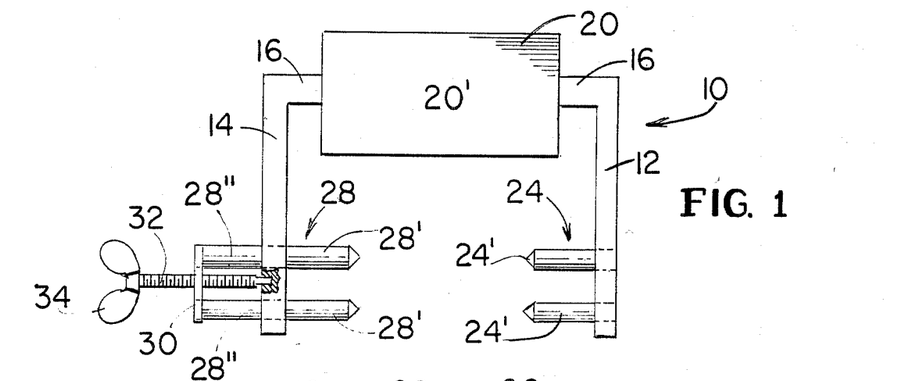
FIG. 1 is a plan view of the device for cutting a patella according to the present invention.

Referring now to the drawing in greater detail, FIG. 1 shows the device for cutting an everted patella, which device is referred to generally by reference numeral 10. The device 10 is a structurally coherent unit in which a pair of leg extensions, or arms, indicated by reference numerals 12 and 14, are provided. Each leg extension 12 and 14 is formed integral with a cross brace indicated generally by reference numeral 16 in FIG. 1. The cross brace 16 mounts a cutting guide support surface indicated generally by reference numeral 20 in FIG. 1. The cutting guide support surface 20 may be formed such that it is permanently affixed to the cross brace 16, or, alternatively, it may be removably but fixedly mounted thereto by any well-known mounting means. It is, also, within the scope and spirit of the present invention to form the cutting guide support surface 20 integral with the cross brace such that the cross brace constitutes two separate arms, each of which has a first end integral with an end of the cutting guide support surface and projects therefrom toward a respective leg extension 12, 14, where its other end is formed integral with the respective extension.

Figure 2:
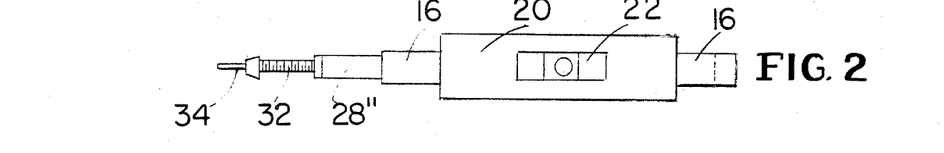
FIG. 2 is a front, elevational view of the device for cutting a patella according to the present invention.

The cutting guide support surface 20 is provided with a level 22 in its front surface, as clearly shown in FIG. 2. The level 22 provides the means by which the cutting guide support surface 20, as well as the rest of the device, may be levelled in a horizontal plane.

The other ends of the leg extensions 12 and 14, which ends are remote and spaced from the ends thereof connected to the cross brace 16, are provided with clamping members. The leg extension 12 is provided with a fixed clamping member 24, which has a pair of pointed prongs 24' for forced insertion into the lateral aspect of a patella. The pair of prongs are preferably formed integral with the ends of the leg extension 12. The prongs 24' of the fixed clamping member 24 are spaced apart a distance to provide ample support of the patella, so that the patella is held firmly and fixedly thereby without movements in planes parallel to the floor and perpendicular thereto.

The end of the leg extension 14 is provided with an adjustable clamping member 28 which is adjustable toward and away from the fixed clamping member 24. The adjustable clamping member 28 is also provided with a pair of pointed prongs 28', each of which has a lateral extending portion 28" projecting on the other side of the leg extension 14 facing away from the fixed clamping member 24. The ends of the projections 28" are connected by mounting plate 30, so that upon movement of the mounting plate 30 in either direction, the prongs 28' move therewith as a unit. Formed in the mounting plate 30 is an opening (not shown) through which is inserted a screw 32 having a head 34. The screw 32 is mounted for stationary rotation in the end of the leg extension 14, between the pair of pointed prongs 28'. The rotational mounting of the screw 32 in the leg extension is well-known, and allows for rotation of the screw but prevents longitudinal axial movement thereof relative to its mounting. Thus, it can be seen in FIG. 1, that upon rotation of the screw 32 in one direction, or the other, the mounting plate, and, therefore, the pointed prongs 28', will move either toward or away from the fixed clamping member 24. The opening formed in the mounting plate 30 is of such size as to have a diameter approximately equal to the basic pitch diameter of the screw 32. Thus, upon rotation of the screw by gripping the head 34, the adjustable clamping member 28 may be adjusted relative to the fixed clamping member 24, to thereby alter the distance therebetween, and, thereby, accomodate patellae of different sizes. Prongs 28' and projections 28" slide through appropriate openings formed in the end of the leg extension 14.

In FIG. 2, it is clearly shown that the upper supporting surface 20' of the cutting guide support surface 20 is elevated above the top surface of the cross brace 16, so that when the clamping members 24 and 28 are clamped to a patella, the plane in which the patella is cut is free from hindrance, when the upper surface 20' is itself used as the support surface for a conventional oscillating saw used to cut the patella, the procedure and method thereof being described in greater detail below.

Since the device must be capable of withstanding the high temperatures of an autoclave, which is used to sterilize instruments, the device of the present invention is preferably made of stainless steel. Also, in the preferred embodiment of the present invention, the length of the cutting guide support surface 20, as measured in a direction from the extension 12 to the extension 14, is 5.0 cm., while the distance from one edge of the cross brace flush with the side surface of the extension 12 to the other edge of the cross brace flush with the side surface of the leg extension 14 is 8.0 cm. Further, the width of the cutting guide support surface 20 in the direction perpendicular to that in which its length is measured is 2.5 cm. In addition, the forward edge surface of the cutting guide support surface 20 is 5 cm. from the very tip of the ends of the leg extensions 12 and 14, which ends mount the clamping members 24 and 28. The width of each leg extension 12 and 14 in a direction taken from one leg extension to the other is preferably 5 mm., which is also the width of the cross brace 16. The thickness of the cutting guide support surface 20, which thickness is shown in FIG. 2, is 1.0 cm.

Before describing the method by which the device of the present invention is utilized to cut an everted patella, it is helpful to first relate the dimensions and shape of a patella with the dimensions of a prosthesis for implantation after a portion of the patella has been cut away by the device of the present invention. The patella is typically of a rounded-base U-shaped configuration, in which the top surface of the "U" would represent the flat, articular surface of cartilage extending from one leg of the "U" to the other leg. The patella itself has a depth, or thickness, ranging between 1.5 cm. and 2.0 cm., as measured from the articular surface to the base, depending upon the size of the person. The layer of cartilage has a depth or thickness of approximately 1 mm. The standard prosthesis, termed colloquially "button", has a depth of 9 mm. with a stem projecting from the bottom thereof of 4 mm., to provide a total depth of 13 mm. for a large and medium size prosthesis. For a small size prosthesis, the depth is 8.5 mm. with a stem of 4 mm. to provide a total depth of 12.5 mm. Since the stem of the prosthesis is force-fitted into a drilled hole in the patella, it can be seen that to provide the same depth to the patella as its original condition, a surgeon would have to remove 9 mm. of the patella for a large or medium size prosthesis, and 8.5 mm. for a small one. Thus, it can be seen that a surgeon must cut off a considerable portion of the patella; at times this portion approaches fully half of the original depth of the patella itself.

It is not always desirable to remove a portion of the patella equal to the depth of the "button", for conditions may prevail with a certain patient that makes it beneficial to remove less than the depth of the button. This would be desirable where it is found that additional tensioning of the tendon is required above that which would prevail if the patella with button were made to be of the same depth as was the original patella. Further, it is very often the case that more than one cut need be made in the patella, if it be found that the first cut did not remove enough of the patella and would thus cause an improper fit against the femur of the patient. Thus, the present invention has provided a method for determining the precise location of the plane of cut in which the oscillating saw will be used, and has provided discreet measuring pieces that allow for the precise location of the plane of cut, and which also allow for easy, simple, and quick repositioning of support surfaces for the conventional oscillating saw to cut through the patella in horizontal planes below that which was previously used for cutting. A conventional oscillating saw is manufactured by, for example, the Zimmer Co. The 3M Company also manufactures an oscillating and reciprocating saw capable of cutting patellae.

Figures 3, 4, 5, 6, 7, 8:
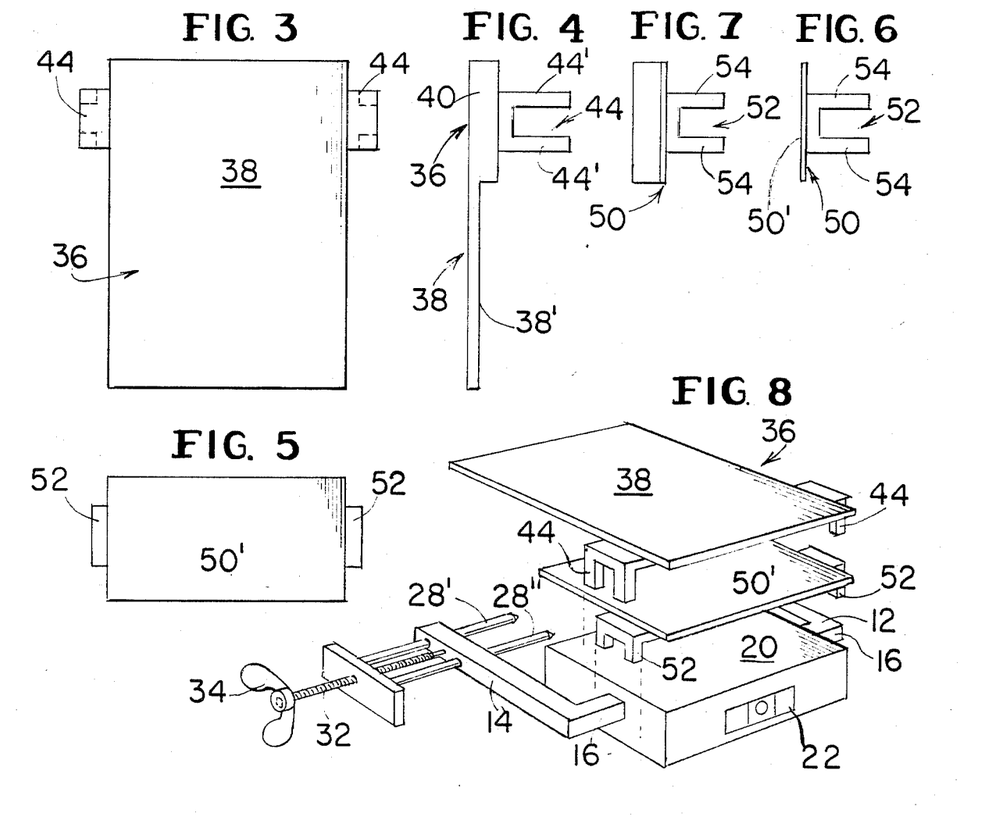
FIG. 3 is a plan view of the placement aid for use with the device for cutting a patella according to the present invention.
FIG. 4 is a side, elevational view of the placement aid of FIG. 3.
FIG. 5 is a plan view of one of the spacers for use with the device for cutting a patella according to the present invention.
FIG. 6 is a side, elevational view of the spacer of FIG. 5.
FIG. 7 is a side, elevational view of a spacer of greater thickness than that of FIG. 5.
FIG. 8 is an assembly view, in perspective, showing the order of assembly of the parts of the present invention.
Figure 9:
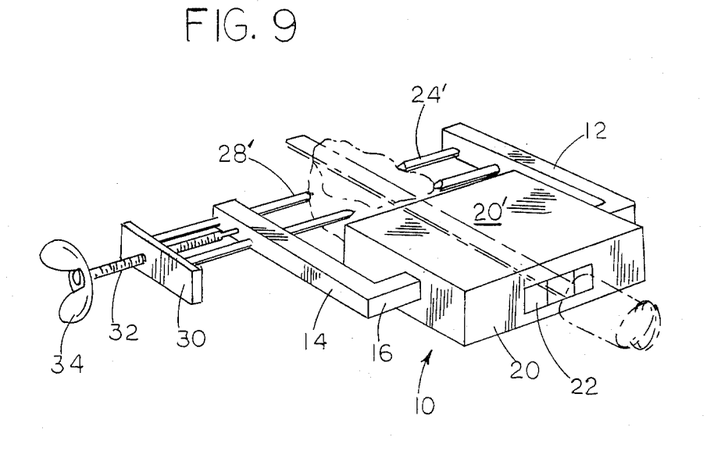
FIG. 9 is a perspective view showing the cutting device of the present invention clamping a patella thereto, with a saw being guided through the patella for cutting.

Toward this end, the present invention is provided with a placement aid indicated generally by reference numeral 36 in FIGS. 3 and 4. The placement aid 36 has an upper projecting positioning surface portion 38 having preferably a thickness of 1 mm. The projecting positioning surface portion 38 has a buttom surface 38' which, when used as described below, is used to rest upon the flat articular surface of the patella held by and between the clamping members 24, 28. The projecting positioning surface portion 38 is provided at its rearward extension with a thicker part indicated by reference numeral 40 in FIG. 4. The bottom surface of the thicker portion 40 is designed to have the same configuration and dimensions as the cutting guide support surface 20; therefore, when the cutting guide support surface 20 has a width of 5 cm. as in the preferred form of the invention, the thicker part 40 also has a width of 5 cm., which width can be seen in FIG. 3. The total projection of the placement aid as measured along the top surface of the projecting surface portion 38 is, in the preferred embodiment of the invention, 7.5 cm., thus giving the upper surface of the placement aid the dimensions of 7.5 cm. by 5 cm. in the preferred embodiment. This projection of 7.5 cm. corresponds with the span of 7.5 cm. from the rear edge of the cutting guide support surface 20 to the tips of te leg extensions 12 and 14, as previously described.

Referring again to FIG. 4, the placement aid 36 is mounted over the cutting guide support surface 20, for flush engagement therewith according to one use of the present invention, by a pair of laterally extending forks indicated generally by reference numerals 44. The forks 44 project downwardly and outwardly from the lateral side edge surfaces of the thicker part 40 of the placement aid, as shown in FIG. 3. Each fork 44 has a pair of fork elements 44' to define therebetween a space in which is received the width of the cross brace 16, so that one fork 44 is mountable to the cross brace at one end of the cutting guide support surface 20, while the other fork 44 is mountable to the cross brace at the other end of the cross brace 16, thereby sandwiching therebetwen the cutting guide support surface, to position the projecting positioning surface portion 38 over the cutting guide support surface 20, as in a stack. The space between the fork elements 44' of each fork 44 is such that it snugly receives the width of the cross brace, so that the movement of the placement aid relative to the cross brace is nonexistant, thereby firmly mounting the placement aid over the cutting guide support surface, and allowing the placement aid to be used as an accurate and precise measure of distance below the articular surface of the everted patella clamped by clamping members 24 and 28. In the preferred form of the invention, the thickness of the placement aid, as measured from the bottom surface of the thicker part 40 to the bottom surface 38' of the projecting positioning surface portion, is 8 mm. Thus, if the placement aid were to be mounted directly over the cutting guide support surface 20 such that they were in contact with each other, so that the bottom surface of the thicker part 40 rested upon the upper surface 20' of the support surface, the distance from the top surface 20' to the bottom surface 38' of the projecting surface portion would be 8 mm., the thickness of the placement aid as described above. Therefore, if one were to mount the placement aid directly over the cutting guide support surface, and were to clamp a patella between the clamping members 24 and 28, such that the bottom surface 38' were made to rest on the articular surface of the everted patella, the distance from the upper surface 20' of the cutting guide support surface below the articular surface would be the 8 mm. described above. Since the thickness of the button to be implanted is 9 mm. for a large and medium-sized patella and 8.5 mm. for a small one, it can be seen that, after levelling the device, the method of which is described below, by removing the placement aid, the upper surface 20' would be precisely 8 mm. below the articular surface, and would provide a support for the oscillating saw used to cut the patella, which would cut the patella in a horizontal plane precisely 8 mm. below the articular surface of the everted patella.

As described above, it is most often the case that the surgeon will make a plurality of cuts through the patella, in order to see each time if the patella with implant has been cut to the desired depth, thus allowing for the minimum removal of patella bone. It is, therefore, desirable to provide a means by which multiple cuts may be made in horizontally level planes, in an easy, precise and concise fashion. This is achieved, according to the present invention, by the provision of what are termed "spacers," one such spacer being shown in FIGS. 5 and 6, and one of greater thickness in FIG. 7 and indicated generally by reference numeral 50. The spacer 50 of FIG. 6 also has a flat surface portion 50' and the spacer of FIG. 7 has a flat surface portion 50" of greater thickness, designed for fitting over the cutting guide surface 20' in the same manner as the placement aid. A pair of forks 52 are also provided, each having a pair of spaced fork elements 54. The forks 54 are used exactly in the same way as the forks 44 of the placement aid 36, and snugly receive the width of the cross brace 16 for mounting the flat surface portion 50' over the upper surface 20'. The forks 54 project out less than forks 44 so that fork 44 may also receive the cross brace. The flat surface portion 50' or 50" has a thickness that will be referred to as the thickness of the spacer for ease of description. In the preferred form of the invention, six such spacers are provided ranging in thickness from 1 mm. to 6 mm., in intervals of 1 mm. One spacer is used at a time in the present invention, and is designed for mounting between the cutting guide support surface 20 and the placement aid, so that when initially setting up the device for use in the preferred form of the invention, the upper surface 20' will be overlaid with one spacer of desired thickness, which, in turn, is overlaid with the placement aid, in a stack formation, with the bottom surfaces of the placement aid and the spacer resting directly on the upper surfaces of the elements therebelow. The fork members 44 of the placement aid are provided with fork elements 44' of sufficient projection from thicker part 40 to accomodate mounting to the cross brace when a spacer is mounted over the cutting guide support surface. FIG. 8 clearly shows the order of arrangement of the parts.

In the preferred form of the invention, the device will start out with a spacer mounted between the placement aid 36 and the cutting guide support surface 20, as shown in FIG. 8, so that after the placement aid has been removed after levelling the device with patella clamped thereto, a series of discreet cutting support surfaces may be provided. The first support surface is provided by the flat surface 50' of the spacer mounted over the cutting guide support surface 20, while up to 5 other support surfaces can be provided by interchanging one spacer for another of smaller thickness. The last support surface, constituting the seventh support surface according to the preferred form of the invention, is achieved by removing the last spacer and exposing the upper surface 20' of the cutting guide support surface. The cutting guide support surface thus provides the maximum depth of cut of the everted patella below the flat articular surface. Thus, if the thickest spacer of 6 mm. shown in FIG. 7 were to be mounted first over the surface 20' between it and the placement aid, then it would provide a plane of cut that is 8 mm. below the articular surface. If it were to be replaced by the 5 mm. thickness spacer, that spacer would allow for a plane of cut 9 mm. below the articular surface, or 1 mm. deeper than that allowed by the 6 mm. spacer. The process can be continued until the right spacer is found that allows for the exact proper cut of the patella below the articular surface, or until the surface 20' provides the proper cut.

It is to be understood that the above dimensions of all of the parts of the device of the present invention are only given by way of example in order to make the understanding of the present invention facile. Other dimensions and configurations may be made, however, without affecting the intent, scope and spirit of the invention, as is clearly plain. The fact that, when using the largest spacer of 6 mm. first over the cutting guide surface 20', it would position the surface 20' 1.4 mm. below the articular surface of the everted patella, which 1.4 mm. is more than half of the depth of the patella, which would just barely leave enough of the patella bone for anchorage of the stem of the prosthesis therein, such is not often found in practice, but allows for the most extreme case where most of the bone of the patella need be removed or has been removed, for whatever reason.

The device of the present invention will be more readily understood by describing the method by which it is used. However, firstly, the method currently utilized by orthopedic surgeons will be described. After the knee joint area has been opened and the patella exposed with its articular surface of cartilage abutting against the femur, the surgeon everts the patella, such that the articular surface is positioned facing upwardly toward the ceiling of the operating room. After this eversion of the patella, one or more assistants will firmly hold the patella by using "towel clips", which are similar in appearance and use to ice tongs. The assistant or assistants will grip the everted patella at a lower portion thereof, so that the surgeon, with the conventional oscillating saw, can freely cut through the patella at a depth below the articular surface that he feels is sufficient for proper implantation of the button, and which will also provide normal functioning of the knee joint. After the surgeon has made the cut in the plane he has chosen, which he has cut through by approximation, without precise and accurate measurements thereof, he will then flip the patella over with the button thereon back to its normal position, so that the flat upper surface of the button now abuts against the femur instead of the original articular surface of cartilage. After this repositioning, the surgeon will check to see if the patella with button thereon fits properly and provides adequate tensioning of the tendon. If, as is most often the case, the surgeon finds that the cut was too narrow or not level or flat, he will evert the patella again, remove the button, cut through the patella bone a second time through a plane below that which was cut through the first time, and then implant the button again; he will then reposition the patella back to its normal position again, to test for a proper functioning and fit a second time. This process is repeated a number of times, until the exact and precise cut is made through the patella to allow for proper functioning and fit. Many of the cuts that are made in the multiple-cut operation of the patella are due to the fact that the bone of the patella is not cut in a flat and horizontal plane, which causes distortions in the normal functioning and positioning of the patella with prosthesis.

The present invention provides a novel method and aparatus that will not only allow for precise cutting of the patella in a perfectly horizontal plane at a desired distance below the articular surface of the patella, but will ensure that all cuts are completely flat, which is a requisite for proper functioning and positioning of the patella. According to the present invention, the first two steps are the same as those presently used, which are to expose the knee joint area to reveal the patella, and then everting it to position the articular surface such that it faces upwardly towards the ceiling in a plane substantially parallel to the floor. Thereafter, according to the present invention, the device having the placement aid with a spacer thereon over the cutting guide support surface is then brought adjacent to the patella such that the bottom surface 38' of the placement aid rests upon the articular surface of the everted patella. At this junction, with the surface 38' resting upon the articular surface, the fixed clamp 24 is forcibly inserted into the lateral aspect of the patella to firmly grip it thereby. After the gripping by the fixed clamping member 24, the cutting guide support surface along with the spacer and placement aid are tilted until the level 22 indicates that all support surfaces lie in a perfectly horizontal plane, at which point, the adjustable clamping member 28 is moved inwardly toward the fixed clamping member 24 to forcibly grip the medial side of the patella. Thus, the device is fixedly attached to the patella such that a series of support surfaces may be readily, easily and precisely exposed to provide cuts in parallel planes progressively deeper. After this initial setting up of the device and clamping of the device to the everted patella, and levelling thereof, the placement aid is removed, thus exposing the upper surface of the flat surface 50' of the spacer 50. This spacer may be the 6 mm. spacer, or any desired spacer having the thickness that the surgeon feels will provide the first cut in a horizontal plane most likely to provide the most suitable results and still ensure that not too much bone has been removed from the patella. To cut off the portion of the patella, the surgeon merely uses the support surface provided by the spacer, and, after the cut has been made in the horizontal plane provided by that spacer, the button is inserted into the patella, which patella with prosthesis is then flipped over to reposition it back to its normal functioning position, where the surgeon will test it for proper fit and proper tensioning of the tendon. If the cut is found to have been made in a horizontal plane too close to the articular surface, so that a deeper cut need be made, he will evert the patella again, remove the prosthesis, exchange the spacer for another of smaller thickness, and repeat the step of cutting and the remainder of the steps above-described. Throughout the whole procedure, the device is clamped to the patella via the clamping members; it is flipped over with the patella and is also everted along with the eversion of the patella for subsequent cuts. For each additional cut made by the surgeon using the oscillating saw, he need only exchange the spacer for another of smaller thickness, so as to cut through the patella in a horizontal plane below that in which the patella was cut in the previous cut. The final deepest cut may be made by removing the spacer and exposing the support surface 20' of the cutting guide support surface, which constitutes the deepest cut possible for the device without reorienting the device with respect to the patella by repositioning the clamping members 24 and 28. By the use of the support surfaces provided by the spacers of the present invention and the support surface 20' of the cutting guide support surface, it is ensured that all cuts are made in perfectly horizontal planes which are completely flat; and it is also ensured that all cuts are made exactly parallel to each other, since the device is held firmly clamped to the patella during all flips and eversions.

The spacers and placement aid, also, preferably made of stainless steel, in order to withstand the high temperatures of an autoclave used for sterilizing equipment used during the operation. Further, while it has been disclosed in the preferred embodiment of the invention that only one spacer may be mounted to the device between the support surface 20' and the placement aid, it is within the spirit, scope, and intent of the present invention to provide a plurality of spacers that are, in fact, stackable one over the other and mountable together on the device over the support surface 20'. In this modification of the invention, the spacers of larger thicknesses may be eliminated, and only those of 1 mm. and 2 mm. would remain, with larger thicknesses being achieved by combinations of the smaller ones.

It is also noted that while it has been shown that the placement aid and the spacers are mountable to the device by forks, it is also within the purview and scope of the present invention to provide other mounting means, such as, for example, a series of pins projecting from the bottom surface of the thicker part 40 of the placement aid and the bottom surface of the flat surface 50' of each spacer. The pins would be appropriately fittable into a corresponding series of holes formed through the support surface 20', as well as through the flat surface 50' of each of the plurality of spacers.

While specific embodiments of the invention have been shown and described, it is to be understood that numerous changes and modifications may be made therein without departing from the scope and spirit of the invention as set out and limited in the appended claims, which embodiments and modifications provide a device and method for cutting a patella for implanation thereto of a prosthesis in a very flexible manner in which a precise cut is made through the patella at an exact and precise location below the articular surface, and which provides for subseqnent cuts therethrough in a flexible and precise and simple fashion that gives the orthopedic surgeon total control over the cutting of the patella. The total control by the orthopedic surgeon is further enhanced by the provision of a handle mounted to the underside of the cutting guide support surface 20, by which the surgeon can grip the device during the cutting procedure.

What is claimed:

1. A device for attachment to an everted patella for providing a horizontally level cutting surface for an oscillating saw used to cut off cartilage of the articular surface of the patella and a layer of bone of desired thickness for subsequent insertion into the patella of a prosthesis, said device comprising:

a first attaching means for removable attachment to a portion of a patella;

a first leg extension having a first end mounting said first attaching means, and a second end remote from said first end;

a second attaching means for removable attachment to another portion of a patella different from that portion to which the first attaching means is attached;

a second leg extension having a first end mounting said second attaching means and a second end remote from said first end; said first and second attaching means being mounted to their respective leg extensions such that they are spaced from each other to define therebetween a space in which is received a patella for attachment to said first and second attaching means;

a cutting support surface means fixedly connected to said second ends of said first and second leg extensions to thereby space said cutting support surface means from said first ends of said leg extensions and, therefore, to space said cutting support surface means from said first and second attaching means, said cutting support surface means defining a guide surface upon which is supportable an oscillating saw used to cut a patella in a cutting plane parallel to said cutting support surface means;

and a placement aid means mountable over said cutting support surface means for allowing the attachment of said first and second attaching means to a patella a desired distance below the articular surface of the patella, said placement aid means having an projecting positioning surface portion that at one end thereof is supportable by the articular surface of the everted patella, and means connected to the other end of said projecting surface portion for spacing said projecting surface portion from said cutting support surface means, whereby after attachment of said first and second attaching means to the everted patella after the distance from the articular surface thereto has been determined by said placement aid means, said placement aid means is removed to expose a cutting surface for an oscillating saw which cutting surface is positioned below the articular surface a desired distance to cut off the desired amount of cartilage and bone.

2. The device according to claim 1, further comprising levelling means for attaching said first and second attaching means to a patella in a horizontal plane.

3. The device according to claim 1, wherein said first attaching means comprises adjustable mounting means, and said first and second attaching means being mounted to their respective leg extensions in a diametrically opposed relationship, said first attaching means being movable toward and away from said second attaching means to alter the distance therebetween, whereby said device may accomodate patallae of various sizes and dimensions.

4. The device according to claim 3, wherein each of said first and second attaching means comprises at least one insertion prong form insertion into a portion of a patella; said adjustable mounting means of said first attaching means comprising a rotatable screw; said at least one insertion prong of said first attaching means having means associated therewith having an opening for matingly receiving said screw, in order to adjust the distance between said first and second attaching means.

5. The device according to claim 3, further comprising levelling means for attaching said first and second attaching means to a patella in a horizontal plane.

6. The device according to claim 1, further comprising at least one spacer for mounting to said cutting support surface means, said at least one spacer comprising a flat surface portion for support upon said guide surface of said cutting support surface means, and means for removably mounting said flat surface portion for support of said flat surface portion upon said guide surface, said flat surface portion defining a thickness thereof used to provide another cutting surface spaced above said guide surface of said cutting support surface means, whereby said flat surface portion may be used to make a first cut in the patella, and thereafter be removed if another deeper cut need be made by using said guide surface itself as the support for the oscillating saw.

7. The device according to claim 6, comprising a plurality of spacers, each of said plurality of spacers having its own flat surface portion and means for removably mounting said flat surface portion; at least one of said plurality of spacers having a thickness different from at least one other of said plurality of spacers, whereby progressively deeper cutting steps may be performed on the patella by interchanging a spacer of one thickness with another spacer of different thickness.

8. The device according to claim 7, wherein there are provided at least one spacer having a thickness of one milmillimeter; at least one spacer having a thickness of 2 milmillimeters; and at least one spacer having a thickness of 3 millimeters.

9. The device according to claim 6, wherein said means for spacing said projecting positioning surface portion of said placement aid means and said means for removably mounting said flat surface portion of said at least one spacer each comprises means removably fixable to said cutting support surface means.

10. The device according to claim 9, wherein said means removably fixable to said cutting support surface means comprises a pair of spaced-apart fork members, said pair of fork members being spaced apart along the width of its respective member in a direction taken from said first attaching means toward said second attaching means; said cutting support surface means comprising a third leg extension and a fourth leg extension, each of said pair of spaced-apart fork members sandwiching therebetween a portion of a respective one of said third and fourth leg extensions for force fitting therewith.

11. The device according to claim 6, wherein said device and said at least one spacer are made of stainless steel.

12. The device according to claim 1, wherein said cutting support surface means comprises a third leg extension having an end connected to said second end of said first leg extension, and a fourth leg extension having an end connected to said second end of said second leg extension; said guide surface being mounted between said ends of said third and fourth leg extensions; and said means for spacing said projecting positioning surface portion from said cutting support surface means comprises means removably fixable to said third and fourth leg extensions on either side of said guide surface.

13. A method for preparing the cutting of an everted patella in a horizontal plane of cut parallel to the articular surface of the patella for removing the cartilage and part of the bone of the patella for subsequent insertion of a prosthesis thereto, in which there is provided a device having a first attaching means and a second attaching means oppositely disposed to the first attaching means, and a cutting support surface spaced from and connected to the first and second attaching means for suport and movement therewith to provide a cutting surface for an oscillating saw used to cut the patella at a desired depth below the flat articular surface, said method comprising the steps of:

(a) affixing the first attaching means of the device to a portion of the patella at a depth below the flat articular surface which portion is below the part of the patella through which the oscillating saw is to cut the patella substantially parallel to the flat articular surface;

(b) levelling the device and its cutting support surface along with the patella articular surface in a horizontal plane; and (c) affixing the second attaching means of the device after said step of levelling the device and cutting suport surface at a portion of the patella substantially diametrically opposite to that portion to which the first attaching means is affixed; whereby the cutting support surface is readied for an oscillating saw to cut the patella at a desired depth thereof in a horizontal plane.

14. The method according to claim 13, wherein the device comprises a placement aid having a projecting positioning surface portion which is provided at one end thereof with a means for mounting the projecting positioning surface portion over the cutting support surface; said step of affixing the first attaching means comprising mounting the placement aid over the cutting support surface such that the projecting positioning surface portion projects outwardly in a direction from the cutting support surface toward the first and second attaching means; conveying the device with placement aid mounted thereon to the location where the everted patella is positioned; placing the forward part of the bottom surface of the projecting positioning surface portion which faces toward the cutting support surface on the articular surface of the everted patella, so that the cutting support surface and the first and second attaching means are positioned below the articular surface of the patella a depth at least equal to the depth of the placement aid as measured from the bottom surface of the projecting positioning surface portion to the cutting support surface when the placement aid is mounted over the cutting support surface; and inserting the first attaching means to a portion of the patella substantially simultaneously with said step of placing the forward part of the bottom surface of the projecting positioning surface portion of the placement aid, whereby the next step of levelling may be carried out.

15. The method according to claim 14, wherein the device also includes a plurality of spacers for mounting over the cutting support surface between the cutting support surface and the placement aid, so as to position the cutting support surface at a greater desired depth below the articular surface of the patella, said step of affixing the first attaching means further comprising mounting one spacer between the cutting support surface and the placement aid prior to said step of mounting the placement aid, whereby the cutting support surface may be positioned below the articular surface a greater depth than that provided by the depth of the placement aid.

16. The method according to claim 14, said step of levelling including adjusting the orientation of the device relative to the first attaching means inserted into a portion of the patella until the cutting support surface is in a horizontal plane; said method further comprising removing the placement aid after said step of affixing the second attaching means.

17. The method according to claim 16, wherein the device also includes a plurality of spacers for mounting over the cutting support surface between the cutting support surface and the placement aid, so as to position the cutting support surface at a greater depth below the articular surface of the patella, said step of affixing the first attaching means comprising mounting one spacer between the cutting support surface and the placement aid prior to said step of mounting the placement aid.

18. The method according to claim 17, wherein said method further comprises the step of removing the spacer to expose the cutting support surface positioned therebelow; said method further comprising supporting an oscillating saw on the cutting support surface, and cutting off in a plane parallel to the cutting support surface a portion of the patella from the articular surface to a desired depth therebelow.

19. The method according to claim 17, further comprising the step of supporting an oscillating saw on the upper surface of the spacer, and cutting off in a plane parallel to the cutting support surface a portion of the patella from the articular surface to a desired depth therebelow.

20. The method according to claim 19, further comprising the step of attaching a prosthesis to the surface of the patella exposed after said step of cutting off; rotating the everted patella with prosthesis and device thereon to its normal position against the femur; thereafter, everting the patella with prosthesis and device thereon; removing the implanted prosthesis from the everted patella; replacing the spacer with another spacer having smaller thickness, so as to position the upper surface of the spacer closer to the cutting support surface; and supporting the oscillating saw on the upper surface of the spacer; and cutting off a second time a portion of the patella from the exposed surface to a desired depth therebelow equal to the thickness of the spacer.

21. A method for cutting off a portion of an everted patella to remove the cartilage thereof and a portion of the bone thereof, comprising the steps of:
(a) firmly holding the everted patella at location below the plane of cut;
(b) mounting a support surface for an oscillating saw to the everted patella in front thereof opposite the portion of the patella where it is firmly held; such that the support surface is positioned below the articular surface of the patella a desired depth;
(c) positioning the everted patella and the support surface in a horizontal plane, said step of positioning comprising the levelling the support surface in a horizontal plane;
(d) supporting the oscillating saw on the support surface at the desired depth below the articular surface; and
(e) cutting through the patella in a horizontal plane to cut off a portion of the patella including the layer of cartilage and part of the bone thereof, whereby a horizontally level cut is made through the patella.

22. The method according to claim 21, wherein said steps of firmly holding the everted patella and mounting a support surface to the everted patella are carried out simultaneously.

23. The method according to claim 21, further comprising adjusting the position of the support surface relative to the portion of the patella at which it is firmly held accomplished during said step of firmly holding; said step of adjusting the position of the support surface comprising adjusting the position in discreet steps so that the support surface can only take on a fixed number of positions relative to the portion of the patella by which the patella is firmly held.

24. The method according to claim 21, further comprising attaching a prosthesis to the everted patella at its cut exposed surface thereof; and repositioning the everted patella to its normal orientation against the femur to test the prosthesis for proper fit.

25. The method according to claim 24, wherein said step of firmly holding the everted patella also comprises firmly holding the patella during said step of attaching a prosthesis and said step of repositioning the everted patella; said steps of firmly holding being carried out such that the patella is firmly held during all steps and during all intervals therebetween.

26. The method according to claim 25, further comprising everting the patella with the prosthesis thereon from its normal position; removing the prosthesis from the patella; adjusting the position of the support surface relative to points where the patella is firmly held to a new position spaced closer to the points where the patella is firmly held, said step of adjusting being carried out in one discreet step; supporting the oscillating saw on the support surface at its new adjusted position; and cutting through the patella a second time in a horizontal plane spaced form the horizontal plane in which the first step of cutting was performed, whereby additional bone of the patella is removed.

27. The method according to claim 21, comprising the step of repositioning the support surface after said step of cutting through; and repeating said steps of repositioning, supporting the oscillating saw, and cutting through a plurality of times until the proper amount of patella has been cut off.

* * * * *